US009429538B2

United States Patent
Eminoglu et al.

(10) Patent No.: US 9,429,538 B2
(45) Date of Patent: *Aug. 30, 2016

(54) METHOD AND APPARATUS FOR BIOCHEMICAL SENSOR ARRAY WITH INTEGRATED CHARGE BASED READOUT CIRCUITRY

(71) Applicants: Selim Eminoglu, Ankara (TR); Haluk Külah, Ankara (TR)

(72) Inventors: Selim Eminoglu, Ankara (TR); Haluk Külah, Ankara (TR)

(73) Assignee: Mikro-Tasarim Elektronik San. ve Tic. A.S., Ankara (TR)

( * ) Notice: Subject to any disclaimer, the term of this patent is extended or adjusted under 35 U.S.C. 154(b) by 173 days.

This patent is subject to a terminal disclaimer.

(21) Appl. No.: 14/089,714

(22) Filed: Nov. 25, 2013

(65) Prior Publication Data

US 2014/0076742 A1 Mar. 20, 2014

Related U.S. Application Data

(63) Continuation of application No. 12/850,551, filed on Aug. 4, 2010, now Pat. No. 8,591,723.

(60) Provisional application No. 61/231,277, filed on Aug. 4, 2009.

(51) Int. Cl.
*G01N 27/26* (2006.01)
*G01N 27/327* (2006.01)

(52) U.S. Cl.
CPC .......... *G01N 27/26* (2013.01); *G01N 27/3275* (2013.01)

(58) Field of Classification Search
None
See application file for complete search history.

(56) References Cited

U.S. PATENT DOCUMENTS

| | | | |
|---|---|---|---|
| 2004/0219069 A1* | 11/2004 | Kalra et al. | 422/99 |
| 2006/0121501 A1* | 6/2006 | Jabs et al. | 435/6 |
| 2007/0298534 A1* | 12/2007 | Ikushima et al. | 438/57 |
| 2008/0035494 A1* | 2/2008 | Gomez et al. | 205/792 |

OTHER PUBLICATIONS

Forsen et al. (Appl. Phys. Lett. 87, 2005).*
CH Instruments (website http://www.chinstruments.com/chi600.shtml 10/, downloaded Oct. 9, 2012).*
Gau et al. (Boisensors & Bioelectronics, 16, 2001, 745-755).*

* cited by examiner

*Primary Examiner* — Jennifer Dieterle
(74) *Attorney, Agent, or Firm* — Snell & Wilmer LLP

(57) ABSTRACT

A MEMS biochemical sensor configured to sense a target molecule, such as a DNA molecule, a protein molecule, and a viruses molecule. The biochemical sensor may include a cell and a readout module. The cell is configured to be coupled to a probe molecule, to retain a pre-sensing charge before the probe molecule is exposed to the target molecule, and to retain a sensing charge after the probe molecule is exposed to the target molecule. The readout module is coupled to the cell and configured to generate a measurement signal based on the pre-sensing charge and the sensing charge.

19 Claims, 9 Drawing Sheets

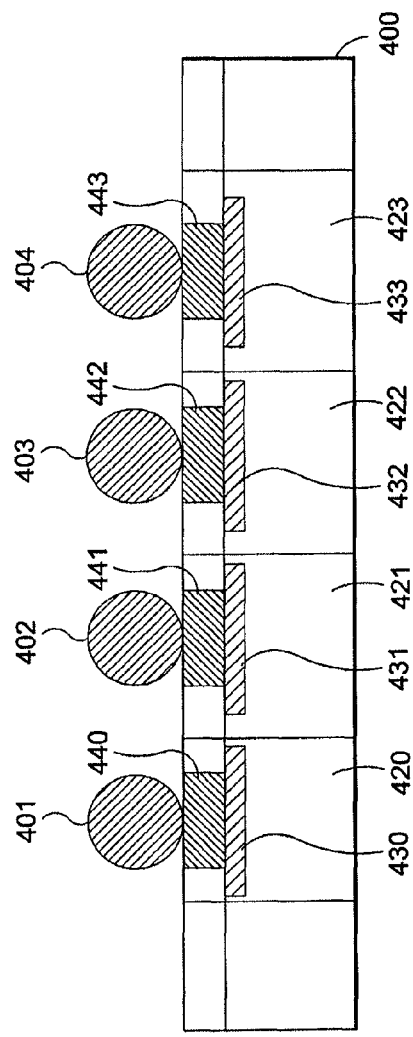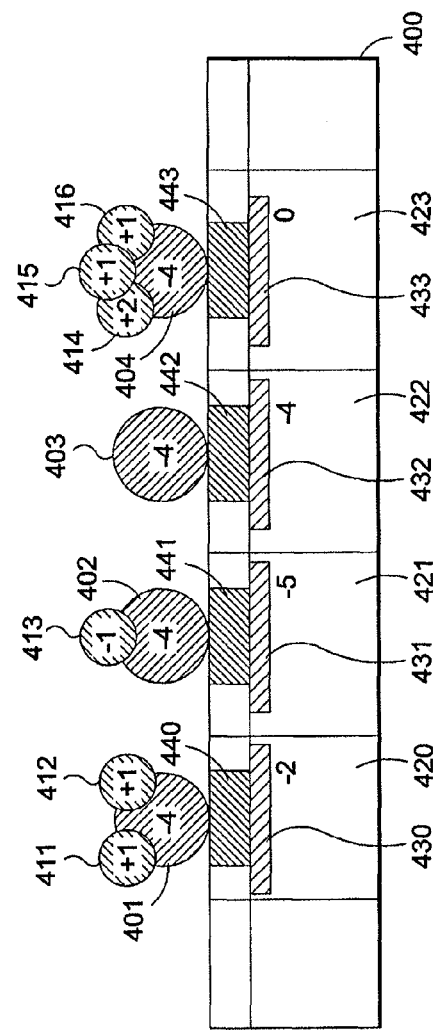

METHOD AND APPARATUS FOR BIOCHEMICAL SENSOR ARRAY WITH INTEGRATED CHARGE BASED READOUT CIRCUITRY

CROSS REFERENCE TO RELATED APPLICATIONS

This application is a continuation of U.S. application Ser. No. 12/850,551, filed Aug. 4, 2010, now U.S. Pat. No. 8,591,723, which claims the benefit and priority to U.S. Provisional Application No. 61/231,277, entitled "METHOD AND APPARATUS FOR BIOCHEMICAL SENSOR ARRAY WITH INTEGRATED CHARGE BASED READOUT CIRCUITRY," filed Aug. 4, 2009, and assigned to the assignee hereof and hereby expressly incorporated by reference herein.

BACKGROUND

1. Field

The present invention relates generally to the fields of biochemical molecule sensing method and apparatus, and more particularly to the fields of Micro-Electro-Mechanical System (MEMS) biochemical molecule sensing system implemented by Complimentary Metal-Oxide Silicon (CMOS) technology.

2. Description of the Related Art

Conventional biochemical molecules (e.g., DNAs, proteins, bacteria, enzymes, viruses, etc.) sensing techniques commonly involve electrochemical sensing and optical sensing. However, electrochemical sensing is generally slow and has poor resolutions, while optical sensing is generally expensive and impractical because it requires elaborate imaging setups.

Attempts have been made in the past to employ electrical sensors to detect or sense biochemical molecules. Potentially, electrical sensing may be faster and cheaper than the electrochemical sensing and optical sensing because it does not require any chemical reaction to take place or any elaborate imaging setups. Nevertheless, electrical sensing has limited sensitivity and limited spatial resolution because the size of each electrical sensor is typically larger than 200×200 $\mu m^2$.

Thus, there is a need for a low cost biochemical sensing system that can provide high speed and high resolution molecule sensing.

SUMMARY

One aspect of the present invention is to provide a low cost, high speed and high resolution biochemical sensor, which may include one sensor cell and an integrated readout module. Another aspect of the present invention is to provide a low cost, high speed and high resolution biochemical sensing system, which may include a sensor array and an integrated readout module. Yet another aspect of the present invention is to provide a method for using the biochemical sensor to achieve low noise real time on-chip sensing.

In an embodiment of the present invention, a MEMS biochemical sensor may include a cell configured to be coupled to a probe molecule, the cell configured to retain a pre-sensing charge before the probe molecule is exposed to the target molecule and to retain a sensing charge after the probe molecule is exposed to the target molecule, and a readout module coupled to the cell and configured to generate a measurement signal based on the pre-sensing charge and the sensing charge.

In another embodiment of the present invention, a MEMS biochemical sensing system may include a plurality of cells, each of the plurality of cells configured to be coupled to one of a plurality of probe molecules, each of the plurality of cells configured to retain a pre-sensing charge before the plurality of probe molecules are exposed to the plurality of target molecules, and configured to retain a sensing charge after the plurality of probe molecules are exposed to the plurality of target molecules, and a readout module selectively coupled to the plurality of cells and configured to generate a plurality of measurement signals, each of the plurality of measurement signals based on the respective pre-sensing charge and the respective sensing charge of one of the plurality of cells.

In yet another embodiment of the present invention, a method for sensing a biochemical molecule may include the steps of coupling a probe molecule to a MEMS biochemical sensor, pre-charging the probe molecule to a bias voltage level, exposing the probe molecule to the biochemical molecule, and detecting, using the MEMS biochemical sensor, a target charge of the biochemical molecule.

BRIEF DESCRIPTION OF THE DRAWINGS

Other systems, methods, features, and advantages of the present invention will be or will become apparent to one with skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

FIG. 4A shows the cross-sectional side view of four sensor cells coupling to four probe molecules according to an embodiment of the present invention;

FIG. 4B shows the cross-sectional side view of four sensor cells coupling to four probing molecules after the probing molecules are exposed to several target molecules;

DETAILED DESCRIPTION

Apparatus, systems, and methods that implement the embodiment of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between reference elements. In addition, the first digit of each reference number indicates the figure in which the element first appears.

Figure 1:
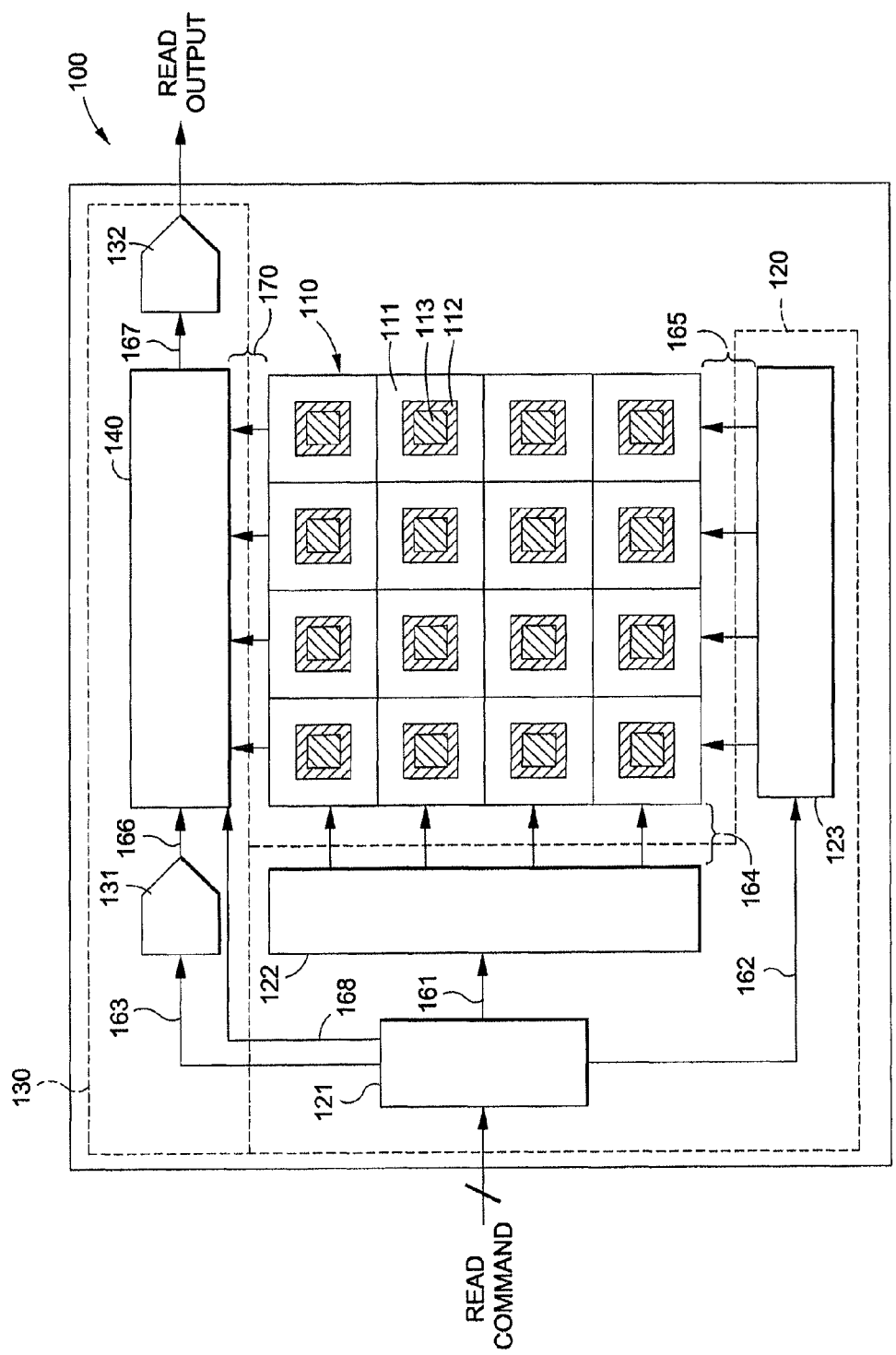
FIG. 1 shows a schematic view of a biochemical system according to an embodiment of the present invention.

FIG. 1 shows a schematic view of a biochemical sensing system (BCSS) 100 according to an embodiment of the present invention. The BCSS 100 may include a sensor array 110, a control module (e.g., a control circuitry) 121, a row select module (e.g., a row select circuitry) 122, a column select module (e.g., a column select circuitry) 123, a biasing module (e.g., a biasing circuitry) 131, a readout module (e.g., a readout circuitry) 140, and an amplifying module (e.g., an amplifying circuitry) 132. The BCSS 100 may be a single chip system such that all the components of the BCSS 100 may be formed on a single substrate. Alternatively, the BCSS 100 may be a multi-chip system such that the BCSS 100 is subdivided and formed on multiple substrates.

Generally, the BCSS 100 may be divided into three subsystems. The first subsystem is the sensor array system (sensor array) 110, which is responsible for sensing or detecting the charges carried by the target biochemical molecules (not shown). The sensor array 110 may contain one or more sensor cells 111, which may be arranged to form several columns and rows. For example, the sensor array 110 may have 16 sensor cells 111, which are arranged to form 4 columns and 4 rows. Each sensor cell 111 may have a first (top) layer 113 and a second (bottom) layer 112. The first layer 113 is responsible for coupling to a probe molecule (not shown) and the second layer 112 is responsible for retaining or sustaining a charge induced by the charge carried by the probe molecule. The sensor cell 111 may also include a sense amplifier (not shown) for converting and amplifying the induced charge to a sensed voltage or a sensed current.

The second subsystem is the logic control system 120, which may include the control module 121, the row select module 122, and the column select module 123. Generally, the logic control system 120 is responsible for controlling the overall operation of the BCSS 100. The logic control system 120 may receive, process, and execute a Read Command. In one instance, the logic control module 120 may initiate a readout operation, select and set a readout mode, and adjust the bias voltages. For example, the control module 121 may be coupled to the biasing module 131 and the readout module 140, so that it may adjust the bias voltage outputs of the biasing module 131 via digital signal 163 and control the timing and readout mode of the readout module 140 via digital signal 168.

In another instance, the logic control system 120 may select one or more sensor cells 111 from the sensor array 110 to be read by the readout module 140. For example, the control module 121 may be coupled to the row select module 122 and the column select module 123, which are ultimately coupled to the sensor array 110. The control module 120 may select one or more rows of sensor cells 111 to be read by controlling the row select module 122 via a row select signal 161. After receiving the row select signal 161, the row select module 122 may couple one or more row nodes 164 to one or more read access nodes 170 such that the readout module 140 may read one or more rows of sensor cells 111. The control module 120 may also select one or more columns of sensor cells 111 to be read by controlling the column select module 123 via a column select signal 162. After receiving the column select signal 162, the column select module 123 may couple one or more column nodes 165 to one or more read access nodes 170 such that the readout module 140 may read one or more columns of sensor cells 111. Practically, the control module 121 may instantaneously select one sensor cell 111, a row of sensor cells 111, a column of sensor cells 111, or an array of sensor cells 111.

The third subsystem is the readout system 130, which may include the biasing module 131, the readout module 140, and the amplifying module 132. Unlike the control system 120, which is mainly digital-based, the readout system 130 is mainly analog-based. For example, the biasing module 131 may be responsible for generating several analog bias voltages 166 for use in the readout operations. For another example, the amplifying module 132 may be implemented by an analog amplifier (not shown) to amplify a measurement signal 167 output by the readout module 140 such that an external device may properly receive the sensing results of the BCSS 100. The readout module 140 may be coupled to one or more sensor cells 111 from the sensor array 110, depending on the connection established by the row select module 122 and the column select module 123. The readout module 140 may instantaneously sense, detect, or read the charge retained by one sensor cell 111, a row of sensor cells 111, a column of sensor cells 111, or an array of sensor cells 111. Alternatively, the readout module 140 may sense, detect, or read the charge retained by multiple sensor cells 111 selected from various rows and columns. After the readout operation, the readout module 140 may output the measurement signal 167, which can be transmitted by a serial bus or a parallel bus.

As discussed earlier, the BCSS 100 may be a multi-chip system. For example, the sensor array system 110, the logic control system 120, and the readout system 130 may be implemented by three distinct chips. For another example, the sensor array system 110 and the logic control system 120 may be implemented by a first chip, which can be combined with a second chip that implements the readout system 130. For yet another example, the sensor array system 110 and the readout system 130 may be implemented by a third chip, which can be combined with a fourth chip that implements the logic control system 120. For still yet another example, the logic control system 120 and the readout system 130 may be implemented by a fifth chip, which can be combined with a sixth chip that implements the sensor array system 110.

Figures 2, 3A, 3B, 3C:
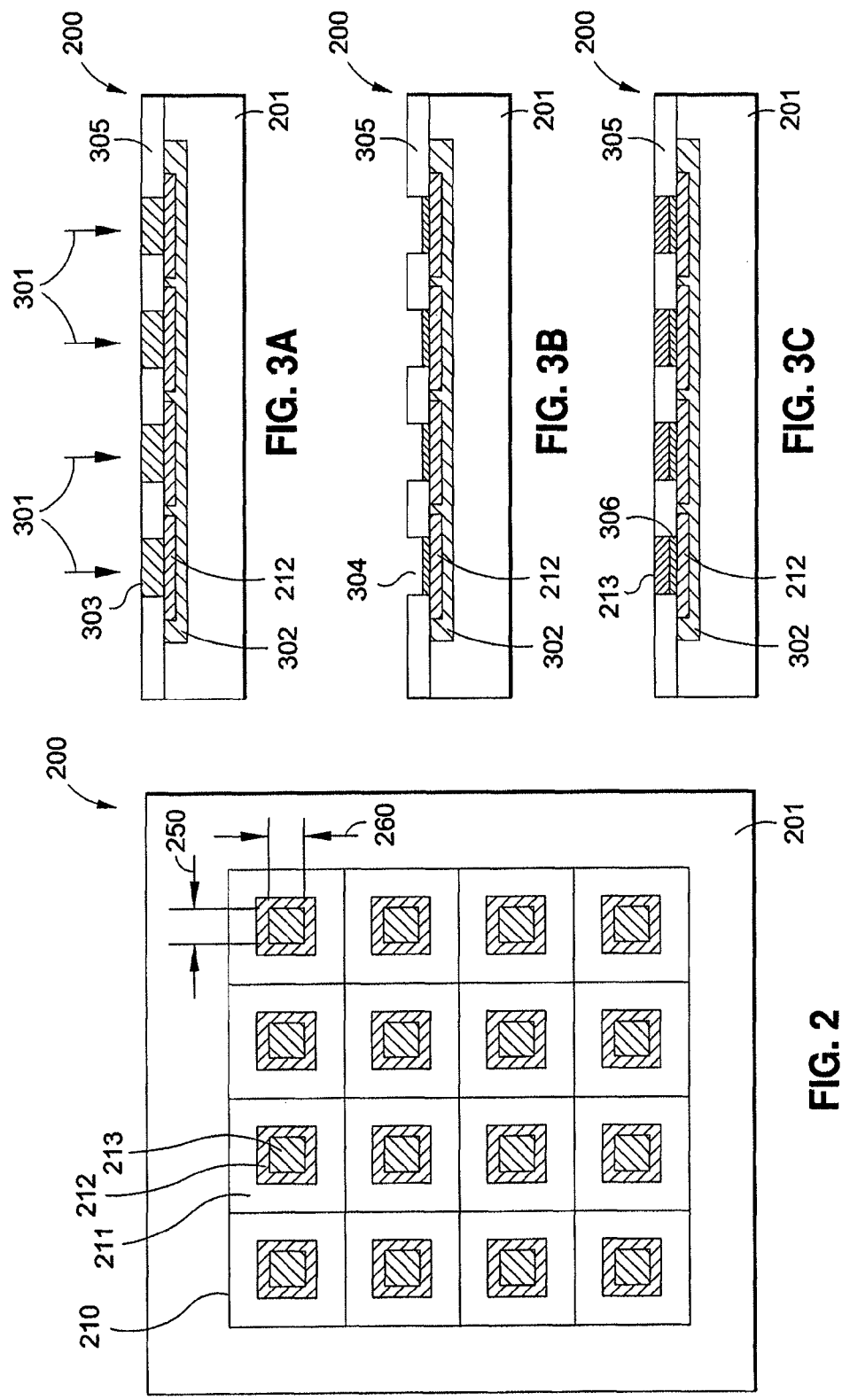
FIG. 2 shows a top view of a sensor array system according to an embodiment of the present invention.
FIGS. 3A-3C show the cross-sectional side views of the sensor array formed on the silicon substrate according to an embodiment of the present invention.

FIG. 2 shows a top view of a sensor array system 200 according to an embodiment of the present invention. The sensor array system 200 may include a sensor array 210 formed on top of a substrate 201. The sensor array 210 may be similar to the sensor array 110 in FIG. 1 such that it may have one or more sensor cells 211, each of which may includes the first layer 213 and the second layer 212. The first layer 213 may have a surface area 214, which has a width 250 and a length 260. According to an embodiment of the present invention, the first layer 213 may have a width 250 and a length 260, both of which may range from about 1.5 um to about 25 um. As such, the surface area 214 of the first layer 213 may range from 2.25 um$^2$ to about 625 um$^2$. Generally, the smaller the surface area 214, the smaller the number of probe molecules (not shown) may be coupled to the first layer 213. As the number of probe molecules per sensor cell 211 decreases, the sensing resolution of the sensor array system 200 increases. For example, the sensor cell 211 may have a resolution ranges from about 1 electron charge to about 5 electron charges. In any event, the sensor area 214 should be kept below about 10 mm$^2$ in order to achieve an efficient cost structure for mass producing the sensor array 210. Depending on the fabrication process used, the number of sensor cells 211 in the sensor array system 200 may range from about 16,384 to about 4,552,931. As the number of sensor cells 211 increases, the spatial resolution of the sensor array system 200 increases. Hence, it is desirable that the sensor array 200 has as many sensor cells 211 as possible and that the surface area 214 of each sensor cell 211 be as small as possible.

FIGS. 3A-3C show the cross-sectional side views of the sensor array 210 formed on the silicon substrate 201 according to an embodiment of the present invention. Referring to FIG. 3A, a well 302 may be developed in the middle of the silicon substrate 201. Typically, the silicon substrate 201 may be formed with silicon based compound and the well 302 may be formed by doping the silicon substrate. The well 302 may delineate and shield the sensor array 210. Within the well 302, the second layers 212 may be deposited using conventional CMOS process. Because a variable amount of charges may be induced and retained in the second layers 212, it is preferable that the second layers 212 to be formed by a conducting material. On top of the well 302 and the second layer 212 is an insulating layer 305, which may be a field oxide deposited by conventional CMOS process. The insulating layer 305 may have several unmasked areas 303, which may be etched away by applying a conventional lithographic process 301.

As shown in FIG. 3B, the unmasked areas 303 results in several openings 304 after the conventional lithographic process 301 is applied to the insulating layer 305. In FIG. 3C, the first layers 213 are deposited within the openings 304 by using a conventional CMOS process. To ensure proper coupling with the probe molecules, it is preferable that the first layers 213 be formed by gold or other materials that may establish good coupling with the probe molecules. Because the first layers 213 are separated from the second layers 212 by the thin insulating layers 306, the second layers 212 may be dielectrically coupled to the first layers 213. As such, when the first layers 213 are coupled to the charged probe molecules, the second layers 212 may retain the same amount of opposite charges. Although FIGS. 3A-3C show that the second layers 213 are floating for the sake of simplicity, there may be interconnecting wires (not shown) coupling the second layers 213 to the row select module 122, the column select module 123, and the readout module 140 as shown in FIG. 1. Accordingly, the charges retained in the second layers 212 may be sensed, read and processed by the readout module 140. Moreover, each of the sensor cells 211 may be coupled to either a conventional voltage-mode input stage device (not shown) or a conventional charge-mode input stage device (not shown) before coupling to the interconnecting wires.

The discussion now turns to the coupling between the sensor cells and the probe molecules and the coupling between the probe molecules and the target biochemical molecules. FIG. 4A shows the cross-sectional side view of four sensor cells 420, 421, 422, and 423 coupling to four probe molecules 401, 402, 403, 404 according to an embodiment of the present invention. Initially, the sensor array system 400 may be exposed to a solution containing the probe molecules 401, 402, 403, and 404. This process may be achieved by forming several micro-fluidic channels on top of the sensor array system 400. As the solution circulates across the micro-fluidic channels, the probe molecules 401, 402, 403, and 404 may be coupled to the first layers 440, 441, 442, and 443. According to an embodiment of the present invention, the probe molecule may be any biochemical molecule that is capable of coupling to the first layer of the sensor cell. For example, the probe molecule may be a DNA molecule and/or a protein molecule.

After the initial coupling, the control module 121 may instruct the biasing module 131 to perform a reset operation, which may pre-charge the probe molecules 401, 402, 403, and 404 to a bias voltage level. This reset operation may serve two purposes. First, it may unify the amount of charges carried by the probe molecules 401, 402, 403, and 404. As a result, the reset operation may minimize the electrostatic noise introduced by these probe molecules and other correlated sources. Second, the pre-charged probe molecules 401, 402, 403, and 404 may become more attracted to the target biochemical molecules (TBMs) because they are oppositely charged. After the reset operation, the readout module 140 may perform a pre-sensing read operation to ensure that the probe molecules 401, 402, 403, and 404 are properly pre-charged. Alternatively, the control module 121 may skip the reset operation and instruct the readout module 140 to read or measure the pre-sensing charges retained by the second layers 430, 431, 432, and 433. These pre-sensing charges may be representative of the amount of charges carried by the probe molecules 401, 402, 403, and 404.

After the pre-sensing read operation, the sensor cells 420, 421, 422, and 423, along with the probe molecules 401, 402, 403, and 404, may be exposed to a solution containing the TBMs. Similar to the process of coupling the probe molecules to the sensor cells, this process may be achieved by forming several micro-fluidic channels on top of the sensor array system 400. As the solution circulates across the micro-fluidic channels, the TBMs may be coupled to the probe molecules 401, 402, 403, and 404. Referring to FIG. 4B, two TBMs 411 and 412 are coupled to the probe molecule 401, one TBM 413 is coupled to the probe molecule 402, no TMB is coupled to the probe molecule 403, and three TBMs 414, 415, and 416 are coupled to the probe molecule 404.

When the probe molecules are coupled to the TBMs, the charges carried by the TBMs may be transferred to the probe molecules, thereby reinforcing or cancelling the initial charges carried by the probe molecules. For example, assuming that the probe molecule 401 carries 4 negative charges and the TBMs 411 and 412 each carries 1 positive charge, the coupled probe molecule 401 may carry only 2 negative charges. For another example, assuming that the probe molecule 402 carries 4 negative charges and the TBM 413 carries 1 negative charge, the coupled probe molecule 402 may carry 5 negative charges. For yet another example, assuming that the probe molecule 404 carries 4 negative charges and the TBMs 414, 415, and 416 carry a total of 4 positive charges, the coupled probe molecule 404 may have 0 charges.

As the charges carried by the probe molecules 401, 402, and 404 change, the second layers 430, 431, and 433 may retain a new set of sensing charges. The sensing charges may directly reflect the electrostatic interaction between the probe molecules and the TBMs, and it may indirectly reflect the amount of target charges carried by the TBMs. Hence, after the sensor array 400 has been exposed to the TBM solution for a period of time, the control module 121 may instruct the readout module 140 to perform another read operation to sense, detect and measure the sensing charges.

Besides the correlated noise introduced by the probe molecules, there is uncorrelated noise introduced by the TBMs and the active circuitry surrounding the sensor array 400. To minimize the uncorrelated noise, the readout module 140 may perform a multiple-read operation at a sampling frequency ranges from about 0.5 MHz to about 10 MHz for each sensor cell. The readout module 140 may then obtain a sensing charge reading by averaging these sample readings. Because the noise among multiple readings is likely to be uncorrelated, this sampling and averaging process may reduce the overall uncorrelated noise level.

Figure 5:
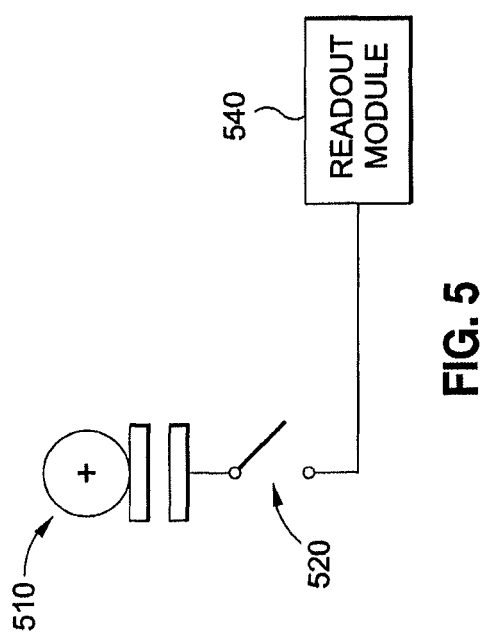
FIG. 5 shows a schematic view of a sensor cell coupled to the readout module according to an embodiment of the present invention.

The discussion now turns to the coupling between the sensor cell and the readout module 140. Although FIG. 1 shows that all the sensor cells 111 of the sensor array 110 share a single readout module 140, the readout module 140 may be incorporated in the sensor array system such that each sensor cell may have its own readout module. For example, FIG. 5 shows a schematic view of the sensor cell 510 coupled to the readout module 540 via a switch 520 according to an embodiment of the present invention. The purpose of the switch 520 is to allow selective coupling between the sensor cell 510 and the readout module 540. When the switch 520 is turned on, the readout module 540 may access the charges retained by the sensor cell 510, and when the switch 520 is turned off, the sensor cell 510 may be isolated from the readout module 540. As such, the switch 520 may be implemented using a conventional CMOS pass gate or other similar electronic components having functionalities consistent with the purpose of the switch 520. The advantages of this one-to-one configuration may include fast readout time and low parasitic noise because of the reduction of interconnecting wires. However, this one-to-one configuration may become more difficult to implement as the number of sensor cells increases.

Figure 6:
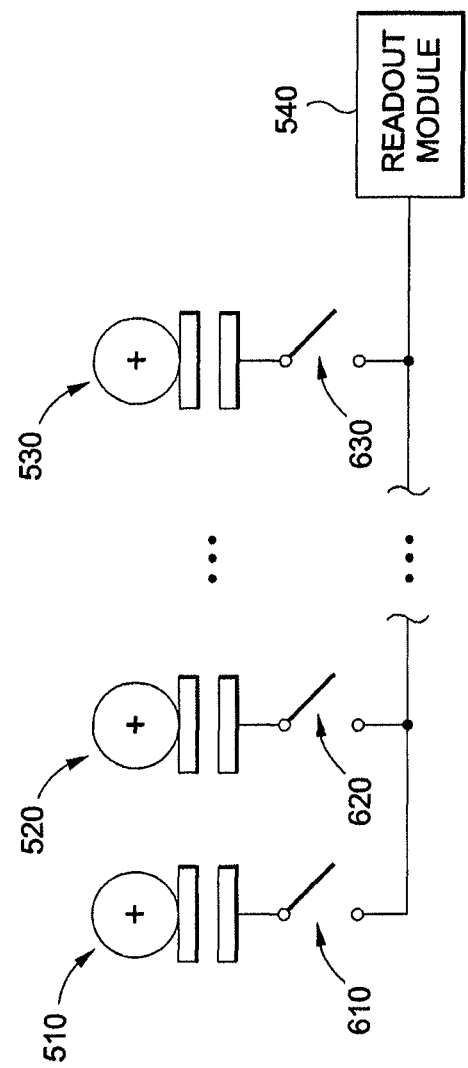
FIG. 6 shows a schematic view of a row of sensor cells coupled to the readout module according to an embodiment of the present invention.

For another example, FIG. 6 shows a schematic view of a row of sensor cells 510, 520, and 530 coupled to the readout module 540 via the switches 610, 620, and 630 according to an embodiment of the present invention. In this row configuration, the row of sensor cells 510, 520, and 530 may share one readout module 540. Hence, only one sensor cell may be coupled to the readout module 540 at a single moment of time. As such, the column select module 123 in FIG. 1 may selectively turn on one of the switches 610, 620, and 630 at a time so that the readout module 540 may detect, sense and measure the charges retained by the sensor cells 510, 520, and 530 in a serial manner. Similar to the switch 520 in FIG. 5, the switches 610 may be implemented by conventional CMOS pass gates or other similar electronic components having functionalities consistent with the purpose of the switches 610, 620, and 630.

Figure 7:
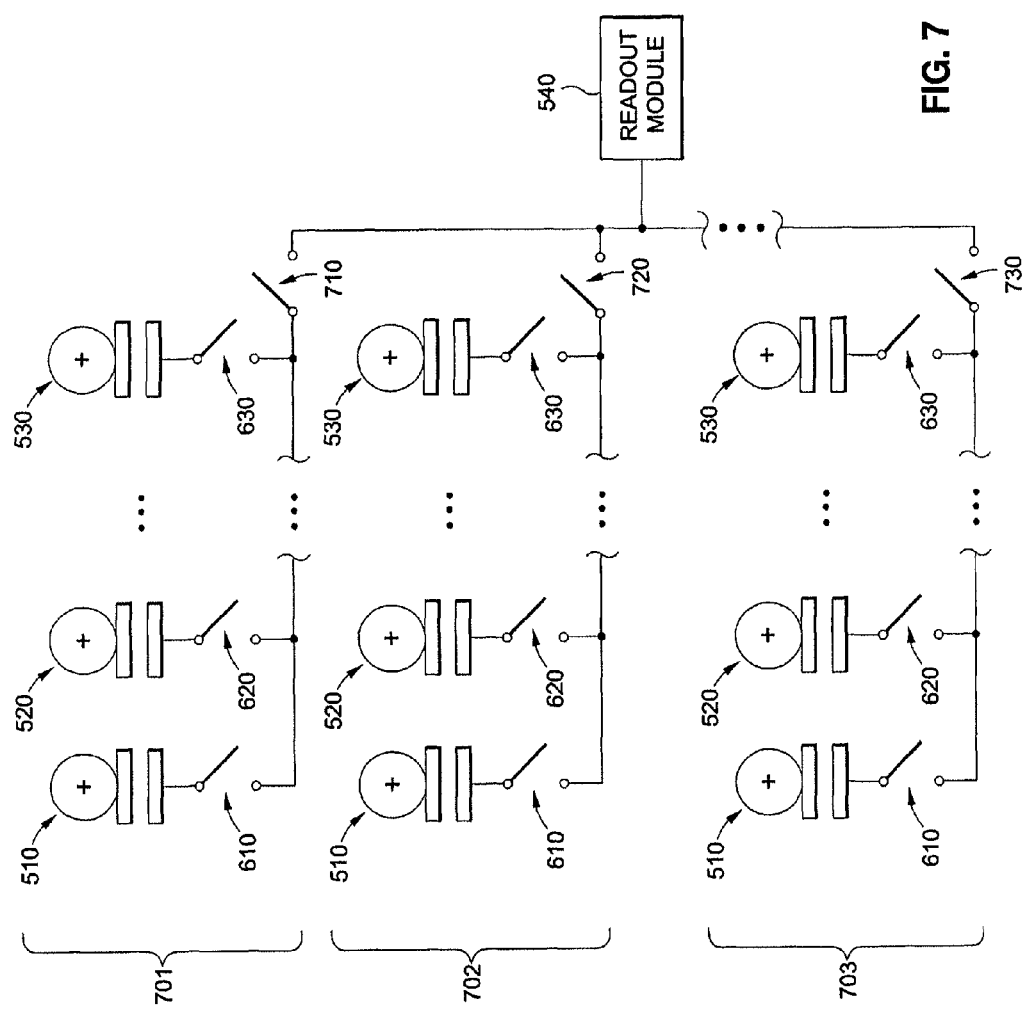
FIG. 7 shows a schematic view of several rows of sensor cells coupled to the readout module according to an embodiment of the present invention.

For yet another example, FIG. 7 shows a schematic view of several rows of sensor cells coupled to the readout module according to an embodiment of the present invention. The rows 701, 702, and 703 are similar to the row configuration shown in FIG. 6, so that the discussion regarding FIG. 6 may apply to each row individually. In this plane configuration, the sensor cells in rows 701, 702, and 703 may share one readout module 540. Hence, only one row of sensor cells may be coupled to the readout module 540 at a single moment of time. As such, the row select module 121 in FIG. 1 may selectively turn on one of the switches 710, 720, and 730 at a time so that the readout module 540 may detect, sense and measure the charges retained by the sensor cells in rows 701, 702, and 703 in a serial manner. Similar to the switch 520 in FIG. 5, the switches 710, 720, and 730 may be implemented by conventional CMOS pass gates or other similar electronic components having functionalities consistent with the purpose of the switches 710, 720, and 730.

Figure 8:
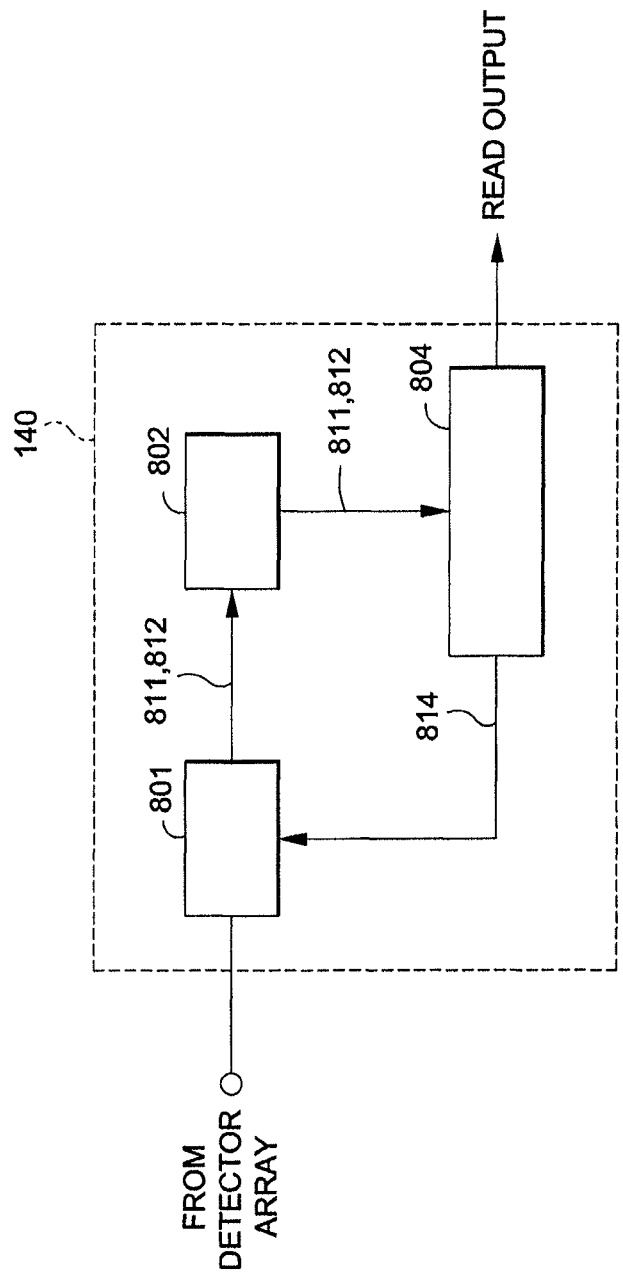
FIG. 8 shows a schematic view of the readout module according to an embodiment of the present invention.

The discussion now turns to the internal components of the readout module 140. FIG. 8 shows a schematic view of the readout module 140 according to an embodiment of the present invention. The readout module 140 may include a sensing device 801, a register 802 and a processor 804. The sensing device 801 may serve two functions. First, the sensing device 801 may receive the charge retained by one of the sensor cells. For example, the sensing device 801 may receive the pre-sensing charges retained by the sensor cells before the probe molecules are exposed to the solution containing the TBMs. For another example, the sensing device 801 may receive the sensing charges retained by the sensor cells after the probe molecules are exposed to the solution containing the TBMs.

Second, the sensing device 801 may generate a pre-sensing signal 811 and a sensing signal 812 based on the received pre-sensing charges and the sensing charges respectively. More specifically, the sensing device 801 may generate two analog signals with voltage levels representing the amount of charges retained by the sensor cells before and after probe molecules are exposed to the solution containing the target molecules. Alternatively, the sensing device 801 may generate two digital signals with digital values representing the amount of charges retained by the sensor cells before and after the probe molecules are exposed to the solution containing the target molecules. In any event, the sensing device 801 may include a conventional CMOS sense amplifier (not shown) that can sense and amplify either the amount of accumulated charges or the small signal current induced by a change of charge. In the event that the pre-sensing signal 811 and the sensing signal 812 are in digital form, the sensing device 801 may also include an analog-to-digital converter. Moreover, because the sensing device 801 may include several analog components, it may receive the necessary biasing voltages from the biasing module 131 as shown in FIG. 1.

Although FIG. 8 shows that the readout module 140 only has one sensing device 801, the readout module 140 may have more than one sensing devices 801, such that more than one sensor cell can be sensed at a single moment of time. For example, the readout module 140 may dedicate sufficient amount of sensing devices 801 for a row of sensor cells or a column of sensor cells.

The register 802 may receive and store the pre-sensing signal 811 and sensing signals 812 generated by the sensing device 801 before the processor 804 may process these signals. The register 802 may be implemented either as a digital register or an analog register, depending on the form of the pre-sensing and sensing signals 811 and 812 generated by the sensing device 801.

The processor 804 may implement at least two sensing modes. In a single sensing mode, the processor 804 may calculate the target charges of the TBMs coupled to a particular sensor cell by simply comparing the sensing signal 812 with the pre-sensing signal 811. In a multiple sensing mode, the processor 804 may generate a sampling signal 814, which carries sampling frequency ranges from about 0.5 MHz to about 10 MHz, to control the sensing operation of the sensing device 801. Upon receiving the sampling signal 814, the sensing device 801 may sense the sensing charges of a particular sensor cell for multiple times at the sampling frequency. Each time when a sample is sensed, the sensing device 801 may generate a sensing signal 812 and send it over to the register 802. As such, the sensing device 801 may generate multiple sensing signals 812 for a particular sensor cell after the probe molecules are exposed to the solution containing the TBMs. After the multiple sensing is completed, the processor 804 may access the register 802 to retrieve the multiple sensing signals 812. To minimize the uncorrelated noise, the processor 804 may average the multiple sensing signals 812 to obtain an average sensing signal. Next, the processor 804 may compare the average sensing signal to the pre-sensing signal 811 in calculating the target charges of the TBMs coupled to a particular sensor cell. Finally, the processor 804 may generate a measurement signal or a plurality of measurement signals as the read output of the readout module 140. Generally, each read operation may take about 10 milliseconds.

Figure 9B:
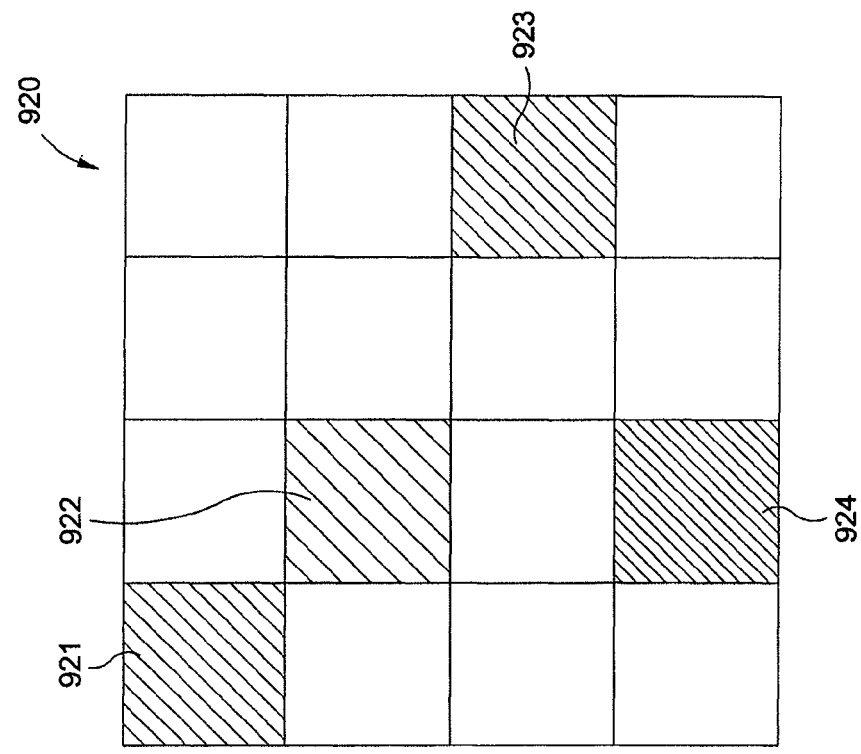
FIG. 9B shows a front view of a computer screen displaying the output of the MEMS biochemical sensor.
Figure 9A:
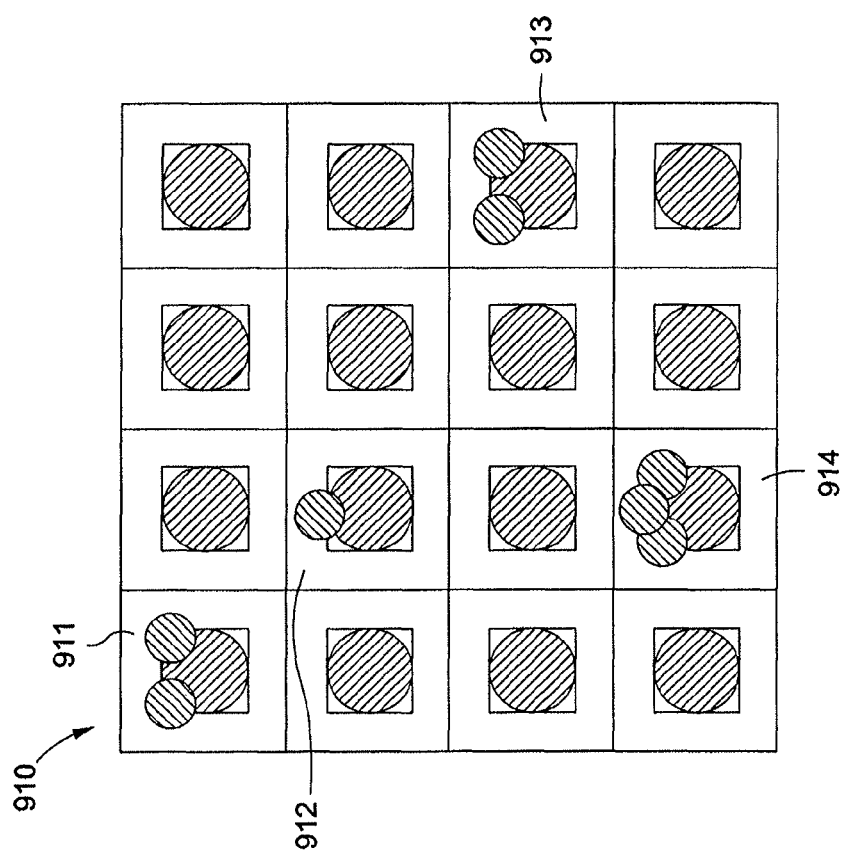
FIG. 9A shows a top view of the sensor array being coupled to the probe molecules and exposed to the target molecules according to an embodiment of the present invention.

The discussion now turns to the output display of the BCSS. As shown in FIG. 9A, the sensor array 910 have four sensor cells 911, 912, 913, and 914 that are coupled to at least one TBMs. After the read operation, the BCSS may output the measurement signal to an external device (not shown) to further process the measurement results. For example, the BCSS may be coupled to a personal computer, which has a processor and a display screen coupled to the processor. As shown in FIG. 9B, the external device may display the measurement results in a grid 920. For example, the boxes 921, 922, 923, and 924 are filled with different colors, such that they may indicate the sensing charges of the respective sensor cells 911, 912, 913, and 914.

Figure 10:
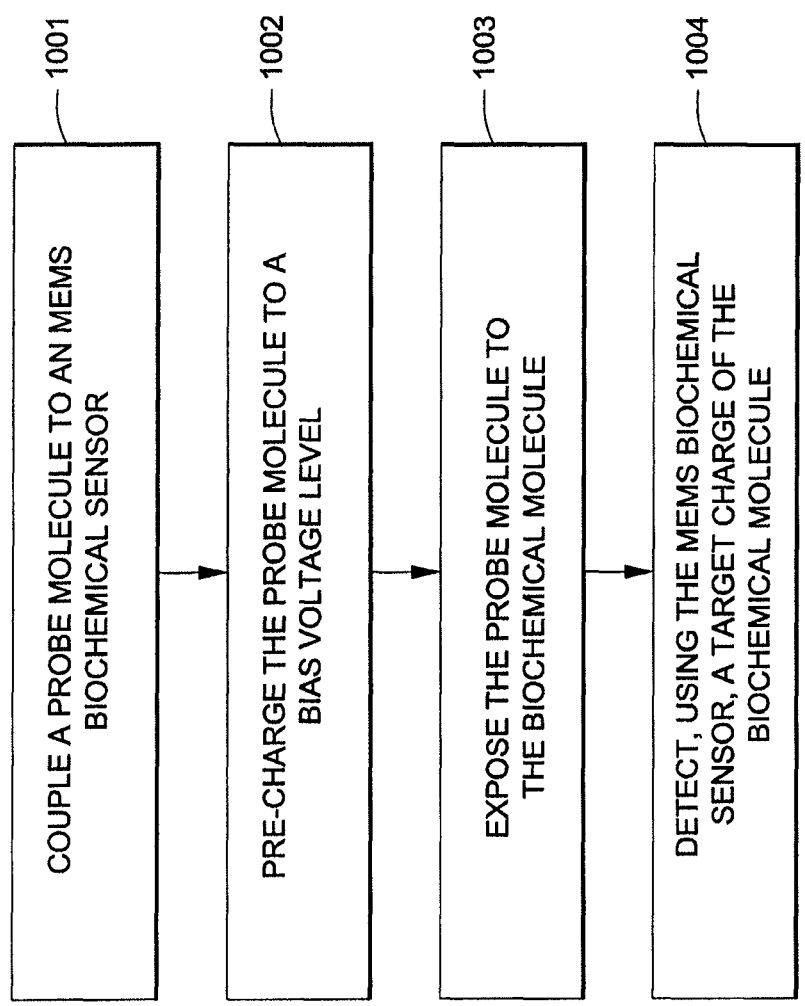
FIG. 10 shows a flow chart of a method for sensing a biochemical molecule by using the MEMS biochemical sensor according to an embodiment of the present invention.

FIG. 10 shows a flow chart of a method for sensing a biochemical molecule by using the MEMS biochemical sensor according to an embodiment of the present invention. These method steps are related to the discussion with respect to FIGS. 1 to 9. Although these steps might introduce terminologies different from those in the previous discussion, these steps are consistent with the spirit and concept of the previous discussion and should not be construed otherwise. In step 1001, a probe molecule may be coupled to a MEMS biochemical sensor. In step 1002, the probe molecule may be pre-charged to a bias voltage level. In step 1003, the probe molecule may be exposed to the biochemical molecule. In step 1004, a target charge of the biochemical molecule may be detected by using the MEMS biochemical sensor.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A MEMS biochemical sensor configured to sense a target molecule, the biochemical sensor comprising:
a sensor array having a plurality of cells that are formed on a MEMS substrate, a respective cell of the plurality of cells being configured to be coupled to a probe molecule, the respective cell being configured to retain a pre-sensing charge before the probe molecule is exposed to a target molecule and to retain a sensing charge after the probe molecule is exposed to the target molecule; and
a readout module on the MEMS substrate and coupled to the respective cell, the readout module being configured to generate a measurement signal based on at least one of the pre-sensing charge of the respective cell or the sensing charge of the respective cell.

2. The sensor of claim 1, wherein the readout module has:
a sensing device coupled to at least one of the plurality of cells and configured to generate a pre-sensing signal based on the pre-sensing charge and to generate a sensing signal based on the sensing charge;
a register coupled to the sensing device and configured to receive and store the pre-sensing signal and the sensing signal; and
a processor coupled to the register and configured to access the register and to generate a measurement signal based on the pre-sensing signal and the sensing signal.

3. The sensor of claim 2, wherein:
the processor is coupled to the sensing device and is configured to generate a sampling signal having a sampling frequency after the probe molecule is exposed to the target molecule,
the sensing device is configured to receive the sampling signal and to generate a plurality of sensing signals at the sampling frequency, and
the register is configured to receive and store the plurality of sensing signals.

4. The sensor of claim 3, wherein the processor is configured to generate an average sensing signal based on the plurality of sensing signals and to generate the measurement signal by comparing the pre-sensing signal and the average sensing signal.

5. The sensor of claim 3, wherein the sampling frequency ranges from about 0.5 MHz to about 10 MHz.

6. The sensor of claim 1, wherein at least one of the plurality of cells has a first layer configured to be coupled to the probe molecule and a second layer dielectrically coupled to the first layer, coupled to the readout module and configured to retain the pre-sensing charge and the sensing charge.

7. The sensor of claim 6, wherein the first layer of at least one of the plurality of cells has a gold surface having an area ranging from about 2.25 $\mu m^2$ to about 625 $\mu m^2$ and configured to be coupled to the probe molecule.

8. The sensor of claim 1, wherein the measurement signal has a resolution that ranges from about 1 electron charge to about 5 electron charges.

9. A MEMS biochemical sensing system configured to sense a plurality of target molecules, the biochemical sensing system comprising:
a chip having:
a plurality of cells, each of the plurality of cells configured to be coupled to at least one of a plurality of probe molecules, to retain a pre-sensing charge before the plurality of probe molecules are exposed to a plurality of target molecules, and configured to retain a sensing charge after the plurality of probe molecules are exposed to the plurality of target molecules; and
a readout module selectively coupled to at least one of the plurality of cells and configured to generate a plurality of measurement signals, each of the plurality of measurement signals being based on the pre-sensing charge and the sensing charge of one of the plurality of cells.

10. The system of claim 9, wherein the plurality of cells is formed as an array having a plurality of rows and a plurality of columns.

11. The system of claim 10, further comprising:
a plurality of column nodes and a plurality of row nodes;
a control module configured to generate a row select signal and a column select signal;
a row select module coupled to the control module and configured to receive the row select signal and to couple at least one of the plurality of row nodes to the readout module based on the row select signal; and
a column select module coupled to the control module and configured to receive the column select signal and to couple at least one of the plurality of column nodes to the readout module based on the column select signal.

12. The system of claim 9, wherein the readout module has:
a sensing device selectively coupled to a respective cell of the plurality of cells and configured to generate a pre-sensing signal based on a respective pre-sensing charge of the respective cell and to generate a sensing signal based on a respective sensing charge of the respective cell;
a register coupled to the sensing device and configured to receive and store the pre-sensing signal and the sensing signal; and
a processor coupled to the register and configured to access the register and to generate a measurement signal based on the pre-sensing signal and the sensing signal.

13. The system of claim 12, wherein:
the processor is coupled to the sensing device and is configured to generate a sampling signal having a sampling frequency after the plurality of probe molecules are exposed to the plurality of target molecules, the sensing device is configured to receive the sampling signal and to generate a plurality of sensing signals at the sampling frequency, and
the register is configured to receive and store the plurality of sensing signals.

14. The system of claim 13, wherein the processor is configured to generate an average sensing signal based on the plurality of sensing signals and to generate the measurement signal by comparing the pre-sensing signal and the average sensing signal.

15. A MEMS cell configured to sense a target molecule comprising:
a first layer configured to be coupled to a probe molecule and then to a target molecule; and
a second layer dielectrically coupled to the first layer such that the second layer is not directly connected to the first layer, the second layer being configured to retain a pre-sensing charge after the first layer is coupled to the probe molecule and to retain a sensing charge that corresponds to a charge carried by the target molecule after the probe molecule is exposed to the target molecule.

16. The MEMS cell of claim 15, wherein the pre-sensing charge corresponds to a charge carried by the probe molecule prior before the first layer is coupled to the target molecule.

17. The MEMS cell of claim 15, wherein the first layer has a surface area ranging from 2.25 micrometers ($\mu$m) to 625 $\mu$m.

18. The MEMS cell of claim 15, wherein the MEMS cell has a resolution that ranges from 1 electron charge to 5 electron charges.

19. The MEMS cell of claim 15, wherein the MEMS cell is formed by:
providing a substrate;
forming a well in the substrate;
forming the second layer in the substrate;
depositing an insulating layer over the second layer; and
depositing the first layer over the insulating layer.

* * * * *